(12) United States Patent
Iketani et al.

(10) Patent No.: US 8,169,466 B2
(45) Date of Patent: May 1, 2012

(54) ENDOSCOPE SYSTEM

(75) Inventors: Kohei Iketani, Saitama (JP); Hideo Sugimoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 596 days.

(21) Appl. No.: 12/394,127

(22) Filed: Feb. 27, 2009

(65) Prior Publication Data

US 2009/0219384 A1 Sep. 3, 2009

(30) Foreign Application Priority Data

Mar. 3, 2008 (JP) ................................. 2008-051625

(51) Int. Cl.
*H04N 13/00* (2006.01)
(52) U.S. Cl. ........................................... 348/45; 348/42
(58) Field of Classification Search .................... 348/42, 348/45
See application file for complete search history.

(56) References Cited

U.S. PATENT DOCUMENTS

| | | | |
|---|---|---|---|
| 6,294,775 B1 | 9/2001 | Seibel et al. | |
| 7,846,091 B2 * | 12/2010 | Fulghum | 600/160 |
| 2002/0161282 A1 | 10/2002 | Fulghum | 600/160 |
| 2005/0059894 A1 * | 3/2005 | Zeng et al. | 600/476 |
| 2005/0177069 A1 * | 8/2005 | Takizawa et al. | 600/573 |
| 2005/0203423 A1 * | 9/2005 | Zeng et al. | 600/476 |
| 2006/0116553 A1 * | 6/2006 | Dunki-Jacobs et al. | 600/179 |
| 2006/0256191 A1 | 11/2006 | Iketani et al. | |
| 2007/0040906 A1 * | 2/2007 | Iketani | 348/69 |
| 2007/0073104 A1 | 3/2007 | Iketani et al. | |
| 2007/0147033 A1 * | 6/2007 | Ogawa et al. | 362/230 |
| 2007/0236782 A1 | 10/2007 | Sano | |
| 2008/0079806 A1 * | 4/2008 | Inuiya et al. | 348/65 |
| 2008/0079807 A1 * | 4/2008 | Inuiya et al. | 348/70 |
| 2008/0200764 A1 | 8/2008 | Okada | |
| 2008/0239070 A1 * | 10/2008 | Westwick et al. | 348/68 |
| 2008/0255426 A1 | 10/2008 | Iketani | |

FOREIGN PATENT DOCUMENTS

JP 2002-34908 2/2002
JP 2005-198794 7/2005

OTHER PUBLICATIONS

English language Abstract of JP 2002-34908, Feb. 5, 2002.
English language Abstract of JP 2005-198794, Jul. 28, 2005.

* cited by examiner

*Primary Examiner* — Liangche A Wang
(74) *Attorney, Agent, or Firm* — Greenblum & Bernstein, P.L.C.

(57) ABSTRACT

An endoscope system comprises a light source, a light sensor, a signal processor, a video-signal generator, and a switcher. The light source emits red light including a first wavelength, green light including a second wavelength, and blue light including a third wavelength. The light sensor receives the light of the light source. The signal processor obtains a red signal based on the red light, a green signal based on the green light, and a blue signal based on the blue light. The video-signal generator generates video signal based on the red, green, and blue signals. The switcher switches between a first switching state and a second switching state. The red, green, and blue signals are output to the video-signal generator in the first switching state. The green and blue signals are output to the video-signal generator in the second switching state.

5 Claims, 9 Drawing Sheets

ENDOSCOPE SYSTEM

BACKGROUND OF THE INVENTION

1. Field of the Invention

The present invention relates to an endoscope system that displays an image based on light including a predetermined wavelength range.

2. Description of the Related Art

An endoscope system that displays an image based on light including a predetermined wavelength range has previously been proposed.

Because the depth from the surface of the tissue from which light is reflected varies according to the wavelength of the illumination light, the desired imaging depth can be adjusted by proper choice of wavelength.

Japanese unexamined patent publication (KOKAI) No. 2002-34908 discloses an endoscope system that displays an image based on light including a predetermined wavelength, by arranging an optical filter that transmits only light of the predetermined wavelength range in the optical path.

However, it takes time to position the optical filter.

Furthermore, when an optical filter is used, an RGB image based on white light illumination can not be obtained. Therefore, in order to switch between an image based on the predetermined wavelength range light and an RGB image, it is necessary to move the optical filter.

SUMMARY OF THE INVENTION

Therefore, an object of the present invention is to provide an endoscope system that outputs an image based on white light and another image based on the predetermined wavelength range light simultaneously, or that is capable of rapidly switching between the display of an image based on white light and the display of an image based on the predetermined wavelength range light.

According to the present invention, an endoscope system comprises a light source, a light sensor, a signal processor, a video-signal generator, and a switcher. The light source has a first emitter that emits red light in a first wavelength range including a first wavelength, a second emitter that emits green light in a second wavelength range including a second wavelength, and a third emitter that emits blue light in a third wavelength range including a third wavelength, and outputs the light from the first emitter, the second emitter, and the third emitter. The second wavelength is shorter than the first wavelength. The third wavelength is shorter than the second wavelength. The first wavelength range does not overlap the second wavelength range. The second wavelength range does not overlap the third wavelength range. The light sensor receives the light of the light source as reflected by the photographic subject, with the light being separated into each wavelength range. The signal processor obtains a red signal based on the light including the first wavelength range, a green signal based on the light including the second wavelength range, and a blue signal based on the light including the third wavelength range, on the basis of the light received by the light sensor. The video-signal generator generates video signal based on at least one of said red signal, the green signal, and the blue signal, obtained by the signal processor. The switcher switches between a first switching estate and a second switching state. The red signal, the green signal, and the blue signal are output to the video-signal generator in the first switching state. The green signal and the blue signal are output to the video-signal generator in the second switching state.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
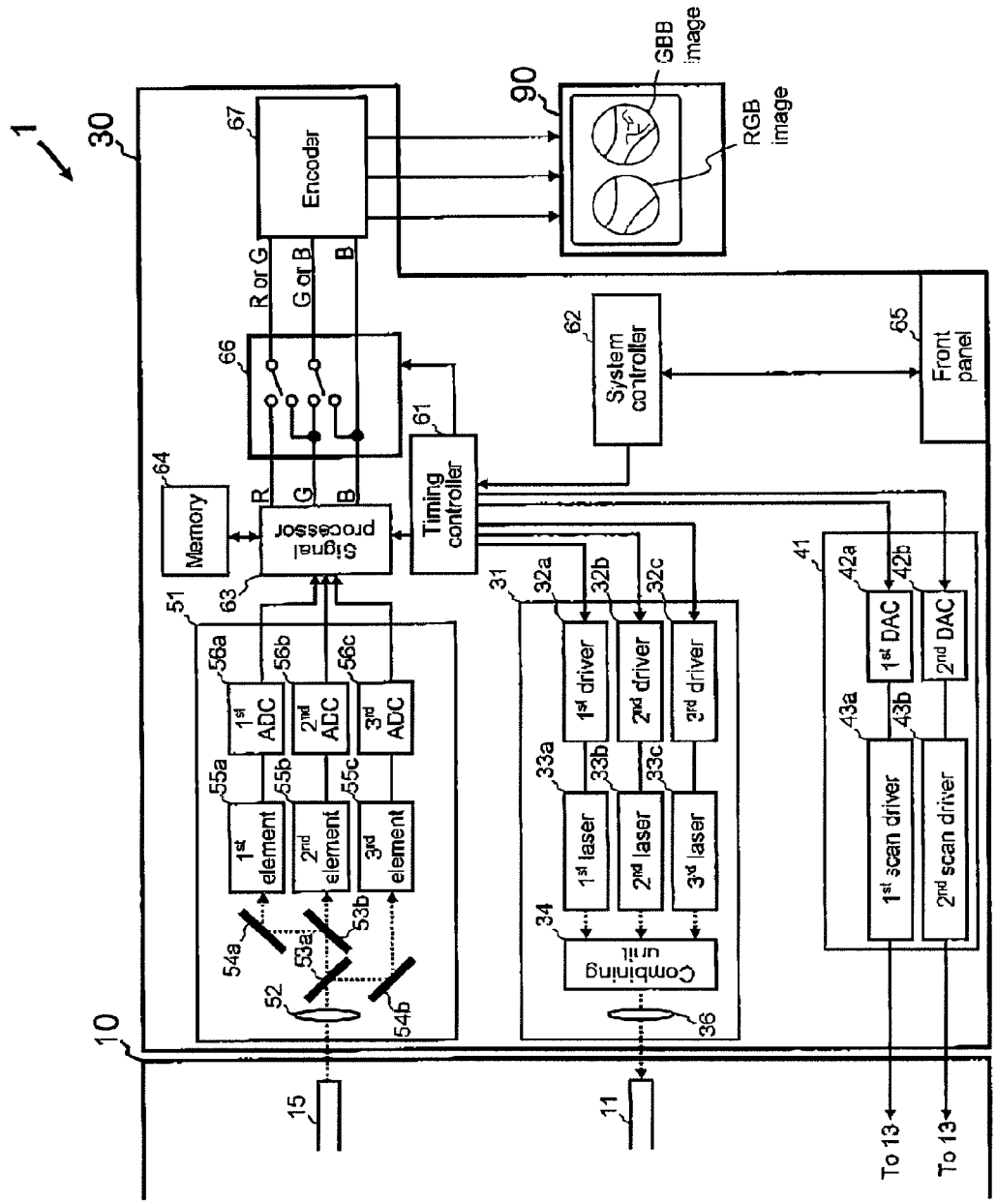
FIG. 1 is a construction diagram of the endoscope system in the first embodiment.

The present invention is described below with reference to the embodiments shown in the drawings (FIGS. 1 to 6). As shown in FIG. 1, an endoscope system 1 in the first embodiment is a full-color scanning fiber endoscope and comprises a probe 10, a processor 30, and a display 90.

Figure 2:
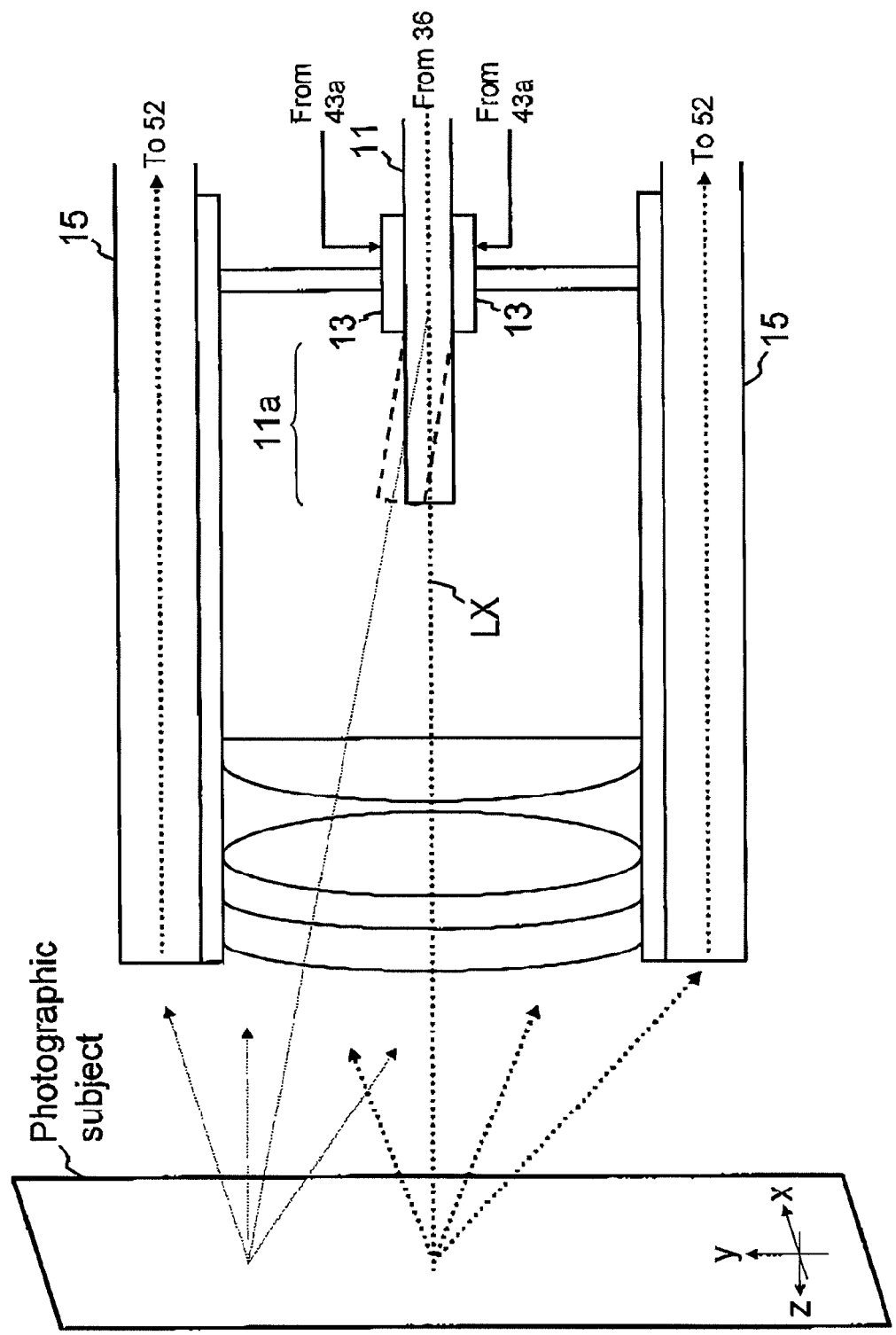
FIG. 2 is a cross-sectional construction diagram of the front tip of the probe.
Figure 3:
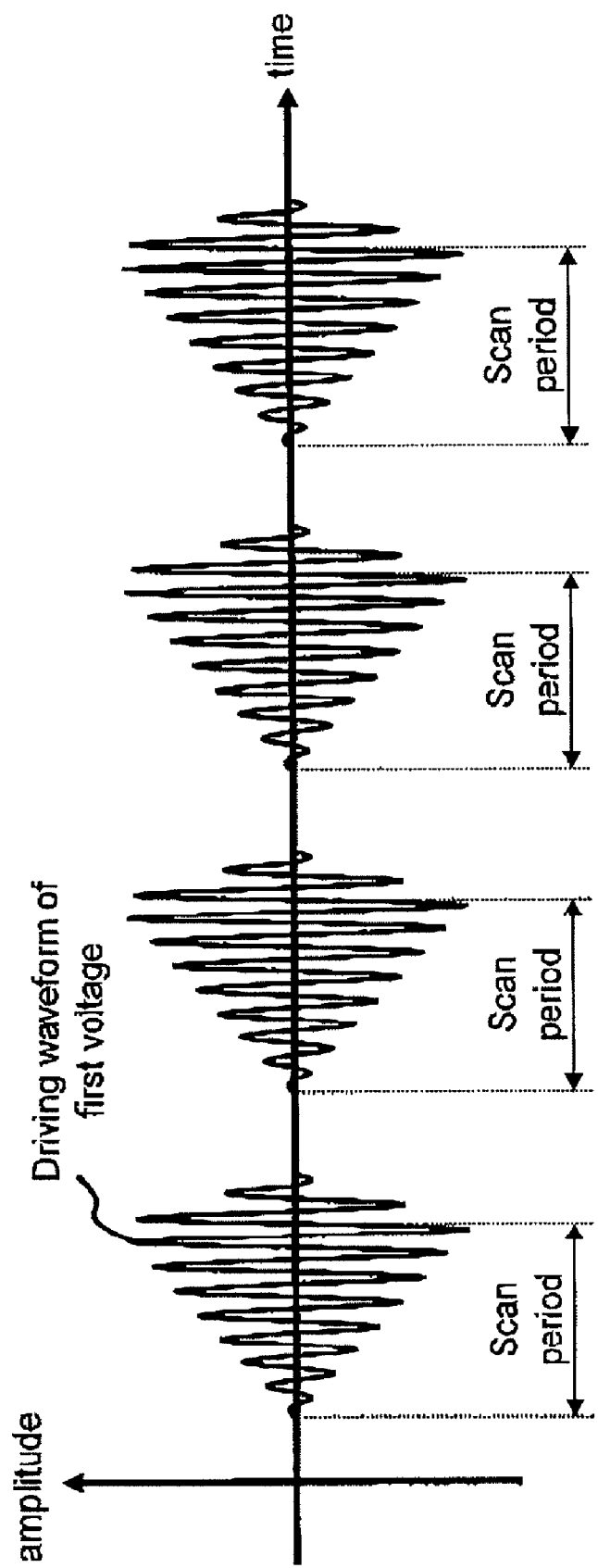
FIG. 3 is a figure that shows a driving waveform of the first voltage.

By way of orientation, in the first and second embodiments, direction x, direction y, and direction z are defined (see FIG. 2). Direction x is the direction perpendicular to the optical axis LX. Direction y is the direction perpendicular to the optical axis LX and direction x. Direction z is the direction parallel to the optical axis LX and perpendicular to both direction x and direction y.

The optical axis LX is the optical axis of an inflexible part of the fiber 11 which is used for illuminating. The inflexible part is not moved or twisted by the scan unit 13, and is arranged at the near side of bendable part of the tip 11a of the fiber 11.

The probe 10 has a fiber 11 for illuminating, a scan unit 13, and fibers 15 for receiving. The fiber 11, which is the scanning fiber, guides light from the light source 31 of the processor 30 to the tip 11a of the fiber 11, and emits light from the tip 11a to the photographic subject which may be the body (tissue) of a patient, etc. Light emitted from the fiber 11 is reflected by the photographic subject and guided to the light sensor 51 of the processor 30 through the fibers 15.

The fibers 15, which are the backscatter return fibers, are arranged around the fiber 11. The scan unit 13 is arranged at the vicinity of the tip 11a of the fiber 11. The scan unit 13 has a piezoelectric device, and oscillates the tip 11a in direction x and in direction y so as to rotate the tip 11a in a spiral when viewed from direction z. The spiral rotation directs the light emitted from the tip 11a of the fiber 11 in a spiral around the optical axis LX as viewed from direction z in so-called spiral track scanning (see dotted arrow in FIG. 5).

The light reflected from the photographic subject, which is emitted from the fiber 11 and whose emission direction changes in a spiral, is guided to the light sensor 51 of the processor 30 through the fibers 15, to form a photographic subject image.

The heavy dotted line in FIG. 2 shows the situation in which white light is emitted from the tip 11a in direction z and then the light reflected by the photographic subject is guide to the light sensor 51 through the fibers 15, in the initial state before the tip 11a is oscillated.

The thin dotted line in FIG. 2 shows the situation in which the bendable part of the tip 11a is twisted so that the tip 11a is moved in direction y and upward from the initial state, and white light is emitted from the tip 11a in the direction that the emission surface of the tip 11a is facing, and then the white light reflects off of the photographic subject.

The processor 30 has a light source 31, a driving unit 41 for scanning, a light sensor 51, a timing controller 61, a system controller 62, a signal processor 63, a memory 64, a front panel 65, a switcher 66, and an encoder (a video-signal generator) 67.

The light source 31 supplies light to the fiber 11 of the probe 10.

The driving unit 41 supplies a control signal to the scan unit 13 of the probe 10.

The light sensor 51 receives the light from the fibers 15. In other words, it receives the reflected light and fluorescence from the photographic subject based on the light from the light source 31, with the light from the fibers 15 being separated into the three wavelength ranges. In addition, the light sensor 51 performs a photoelectric conversion of the incident light.

The processor 30 performs image processing on the image signal based on the light from the fibers 15 of the probe 10, in order to generate and output a video signal to be displayed on the display 90.

The light source 31 has a first driver 32a, a second driver 32b, a third driver 32c, a first laser 33a, a second laser 33b, a third laser 33c, a combining unit 34, and a first condenser lens 36 for illuminating.

The first laser 33a is a rod light laser diode, and emits light in a first wavelength range including a first wavelength $\lambda_R$ on the basis of the control of the timing controller 61, the system controller 62, and the first driver 32a. The first wavelength $\lambda_R$ is about 640 nm, namely, from 630 nm to 650 nm.

The second laser 33b is a green light laser. For example, the second laser 33b may consist of an infrared laser diode together with a wavelength conversion board, and emits light in a second wavelength range including a second wavelength $\lambda_G$ on the basis of the control of the timing controller 61, the system controller 62, and the second driver 32b. The second wavelength $\lambda_G$ is about 540 nm, namely, from 532 nm to 550 nm.

The third laser 33c is a blue laser diode, and emits light in a third wavelength range including a third wavelength $\lambda_B$ on the basis of the control of the timing controller 61, the system controller 62, and the third driver 32c. The third wavelength $\lambda_B$ is about 420 nm (408 nm or 445 nm).

The three wavelength ranges are narrow wavelength ranges and do not overlap.

There are two peak wavelengths at which hemoglobin absorbs light. One is 550 nm, the other is 415 nm. Therefore, when the second wavelength range includes 550 nm or when the third wavelength range includes 415 nm, the blood vessel undergoing growth become clear so that an image clearly distinguishing an affected region from a healthy region may be obtained.

The light paths of the first, second, and third lasers 33a, 33b, and 33c are combined into one by the combining unit 34.

The resulting white light from the combining unit 34 is condensed by the first condenser lens 36 and is transmitted to the fiber 11.

The driving unit 41 for scanning has a first DA converter 42a, a second DA converter 42b, a first scan driver 43a, and a second scan driver 43b.

The first DA converter 42a converts a timing pulse output from the timing controller 61 to an analog signal.

On the basis of the analog signal converted by the first DA converter 42a, the first scan driver 43a drives the scan unit 13 where the tip 11a of the fiber 11 oscillates in direction x.

The second DA converter 42b converts a timing pulse output from the timing controller 61 to an analog signal. On the basis of the analog signal converted by the second DA converter 42b, the second scan driver 43b drives the scan unit 13 where the tip 11a of the fiber 11 oscillates in direction y.

The first scan driver 43a applies a first voltage on a first electrode of the scan unit 13 for driving in direction x. The first voltage has a sinusoidal waveform which is amplified at a predetermined rate for each scan period (about 25 msec; see FIG. 3).

The second scan driver 43b applies a second voltage on a second electrode of the scan unit 13 for driving in direction y. The second voltage has a sinusoidal wave form with the same shape as that of the first voltage and has a phase lag of $\pi/2$ with respect to the first voltage.

The light sensor 51 has a second condenser lens 52 for receiving, a first separation mirror 53a, a second separation mirror 53b, a first mirror 54a, a second mirror 54b, a first light-sensitive element 55a, a second light-sensitive element 55b, a third light-sensitive element 55c, a first AD converter 56a, a second AD converter 56b, and a third AD converter 56c.

The first separation mirror 53a and the second separation mirror 53b separate light of a predetermined wavelength range; for example, a dichroic mirror.

Figure 4:
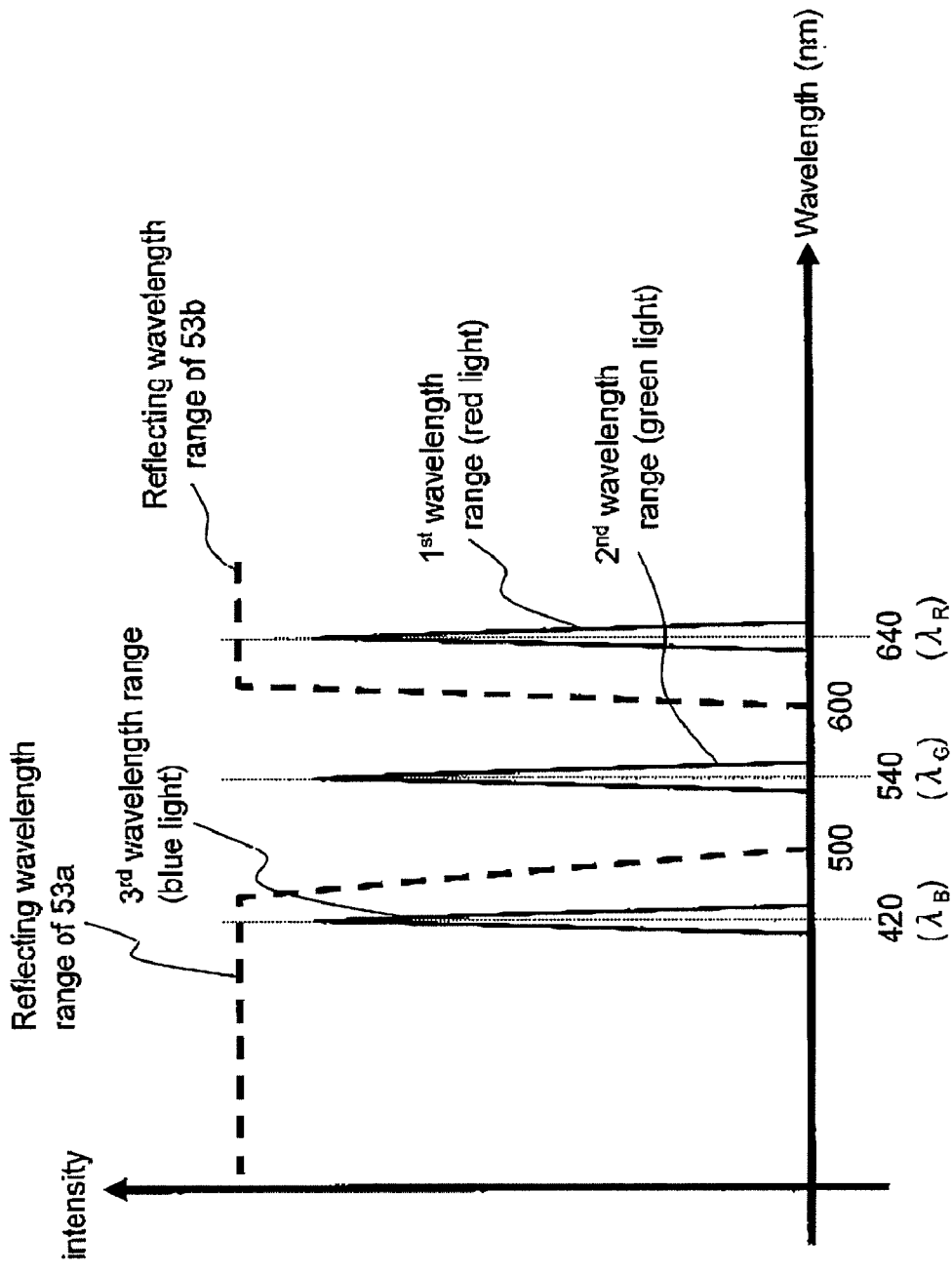
FIG. 4 shows the wavelength ranges of the light output from the first, second, and third lasers.

Short-wavelength light (i.e., blue light of less than 500 nm), in other words, the blue light including the third wavelength range, is reflected by the first separation mirror 53a (see FIG. 4).

The other lights, in other words, the red light including the first wavelength range and the green light including the second wavelength range, pass through the first separation mirror 53a.

Long-wavelength light (i.e., red light of more than 600 nm), in other words, the red light including the first wavelength range, is reflected by the second separation mirror 53b.

The remaining light, in other words, the green light including the second wavelength range, passes through the second separation mirror 53b.

The first light-sensitive element 55a, the second light-sensitive element 55b, and the third light-sensitive element 55c consist of a photodetector such as photomultiplier tube, etc.

The light transmitted from the fibers 1b is converted to a parallel light beam by the second condenser lens 52.

Then, the red light in the parallel light beam reaches the first light-sensitive element 55a through the first separation mirror 53a, the second separation mirror 53b, and the first mirror 54a.

The green light in the parallel light beam reaches the second light-sensitive element 55b through the first separation mirror 53a and the second separation mirror 53b.

The blue light in the parallel light beam reaches the third light-sensitive element 55c through the first separation mirror 53a and the second mirror 54b.

The first light-sensitive element 55a performs the photoelectric conversion on the red light incident on the first light-sensitive element 55a.

The first AD converter 56a performs the AD conversion on the red light incident on the first light-sensitive element 55a after the photoelectric conversion, and then outputs the analog signal of the red light to the signal processor 63.

The second light-sensitive element 55b performs the photoelectric conversion on the green light incident on the second light-sensitive element 55b.

The second AD converter 56b performs the AD conversion on the green light incident on the second light-sensitive element 55b after the photoelectric conversion, and then outputs the analog signal regarding the green light to the signal processor 63.

The third light-sensitive element 55c performs the photoelectric conversion on the blue light incident on the third light-sensitive element 55c.

The third AD converter 56c performs the AD conversion on the blue light incident on the third light-sensitive element 55c after the photoelectric conversion, and then outputs the analog signal regarding the blue light to the signal processor 63.

The timing controller 61 supplies a timing pulse to all parts of the processor 30, based on control by the system controller 62, so as to control the operation of all parts of the processor 30.

In particular, the timing controller 61 supplies the timing pulse for controlling the switching state of the switcher 66, according to the display mode (RGB image display mode, GBB image display mode, or dual display mode) set based on the operation of the front panel 65.

Figure 5:
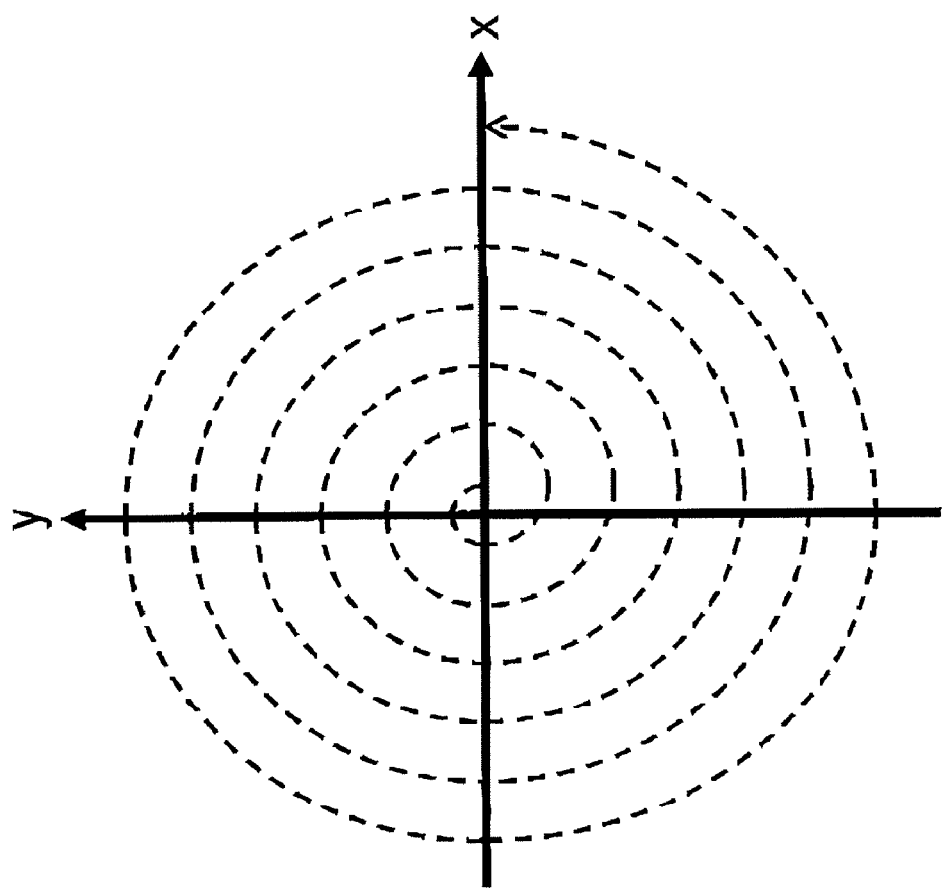
FIG. 5 shows the arrangement order of the first data array before the spiral-raster scan conversion.
Figure 6:
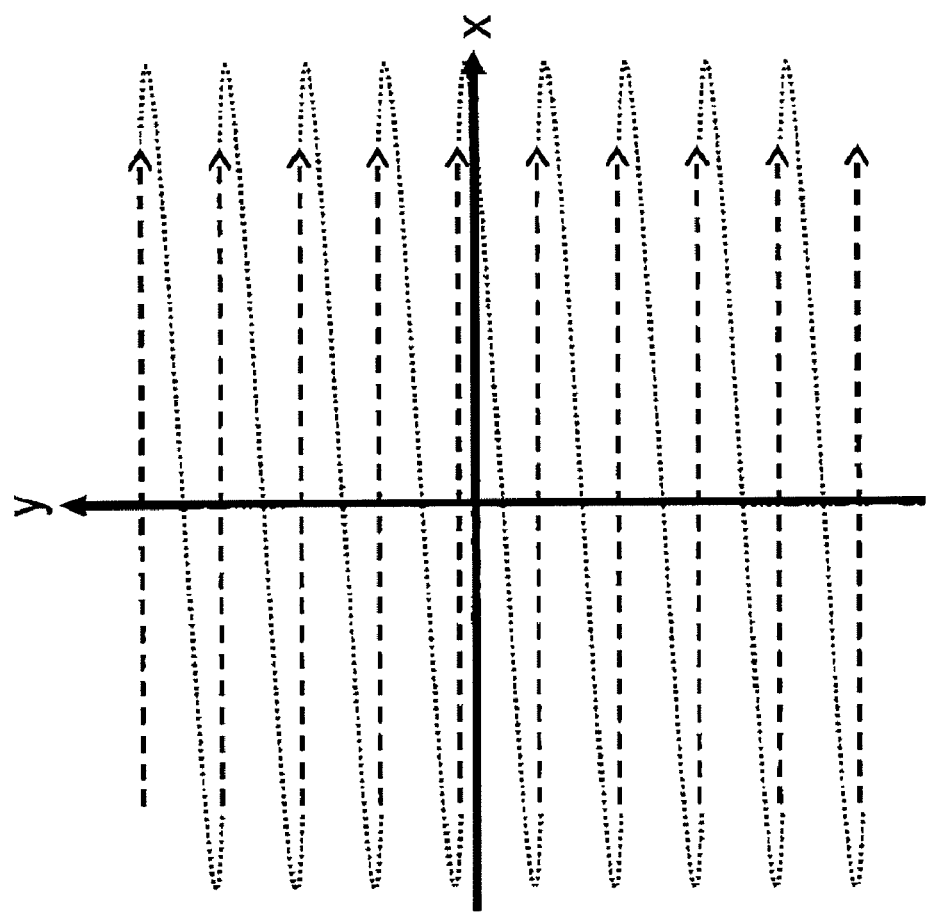
FIG. 6 shows the arrangement order of the second data array after the spiral-raster scan conversion.

The signal processor 63 performs a remapping from a first data array of the imago signal obtained by the spiral track scanning, in other words, the first data array of the image signal of the reflected light that is arranged in the spiral-shaped trace of illumination (see FIG. 5), to a second data array ordered in x-y coordinates (i.e., the spiral-raster scan conversion, see FIG. 6).

Then, the signal processor 63 performs primary image processing on the image signal whose data array is rearranged from the first data array to the second data array, such as gamma correction, edge enhancement, etc.

After the primary image processing, the image signal is temporarily stored in the memory 64.

Then, the signal processor 63 reads the image signal temporarily stored in the memory 64, in separate color signals. Specifically, the signal processor 63 reads the red signal (R signal) based on the red light incident on the first light-sensitive element 55a, the green signal (G signal) based on the green light incident on the second light-sensitive element 55b, and the blue signal (B signal) based on the blue light incident on the third light-sensitive element 55c, and then outputs them to the encoder 67 through the switcher 66.

Thereby, the signal processor 63 obtains the red signal based on the first wavelength range, the green signal based on the second wavelength range, and the blue signal based on the third wavelength range, on the basis of the light received by the light sensor 51.

The switcher 66 performs the switching operation between a first switching state corresponding to the RGB image display mode and a second switching state corresponding to the GBB image display mode.

In the first switching state (in the RGB image display mode), the red signal, the green signal, and the blue signal from the signal processor 63 are output to the encoder 67.

In the second switching state (in the GBB image display mode), the green and blue signals from the signal processor 63 are output to the encoder 67.

The switching operation may be performed by an electrical switching circuit as shown in FIG. 1, however, it may also be performed through software.

In the RGB image display mode where the RGB image based on the red, green, and blue signals is displayed on the display 90, the red, green, and blue signals are output from the switcher 66 to the encoder 67. Specifically, the red, green, and blue signals are output to their respective channels of the encoder 67.

In the GBB image display mode where the GBB image based on the green and blue signals is displayed on the display 90, the green and blue signals are output from the switcher 66 to the encoder 67. Specifically, the green signal is output to the red channel of the encoder 67, and the blue signal is output to the green channel and the blue channel of the encoder 67. Therefore, the red signal does not reach the encoder 67.

In the dual display mode where the RGB image and the GBB image are displayed in parallel on the display 90 (see FIG. 1), the switcher 66 switches to the first switching state during the first half of a display scan line, and to the second switching state during the latter half of the display scan line.

Because the RGB image in the dual display mode is smaller than in the RGB image display mode and the GBB image in the dual display mode is smaller than in the GBB image display mode, the data volume is not increased in the dual display mode compared to the RGB or GBB image display modes even if a combined RGB and GBB image is output.

In other words, the time required for outputting the red, green, and blue signals for displaying the RGB image and for outputting the green and blue signals for displaying the GBB image in the dual display mode is not greater than the time required for outputting the red, green, and blue signals for displaying the RGB image in the RGB image display mode (or the time required for outputting the green and blue signals for displaying the GBB image in the GBB image display mode).

The encoder 67 performs secondary image processing on the image signal from the signal processor 63 through the switcher 66, so as to generate the video signal (the luminance signal and the color-difference signal) for displaying on the display 90, and then outputs the video signal to the display 90.

Therefore, the RGB image as the normal image based on white light and the GBB image, can be displayed simultaneously. In the GBB image, information regarding the blood capillary etc., is clearly displayed compared to the RGB image.

Because the time for switching between the RGB image and the GBB image is not necessary in the dual display mode, the inspection time using the endoscope system 1 can be reduced compared to the case that the RGB image and the GBB image are displayed separately and the RGB image display mode and the GBB image display mode is switched.

Furthermore, in the first embodiment, because the RGB image and the GBB image are displayed on the basis of the same image signal, there is a merit that the time lag for capturing between the RGB image and the GBB image does not occur.

Figure 7:
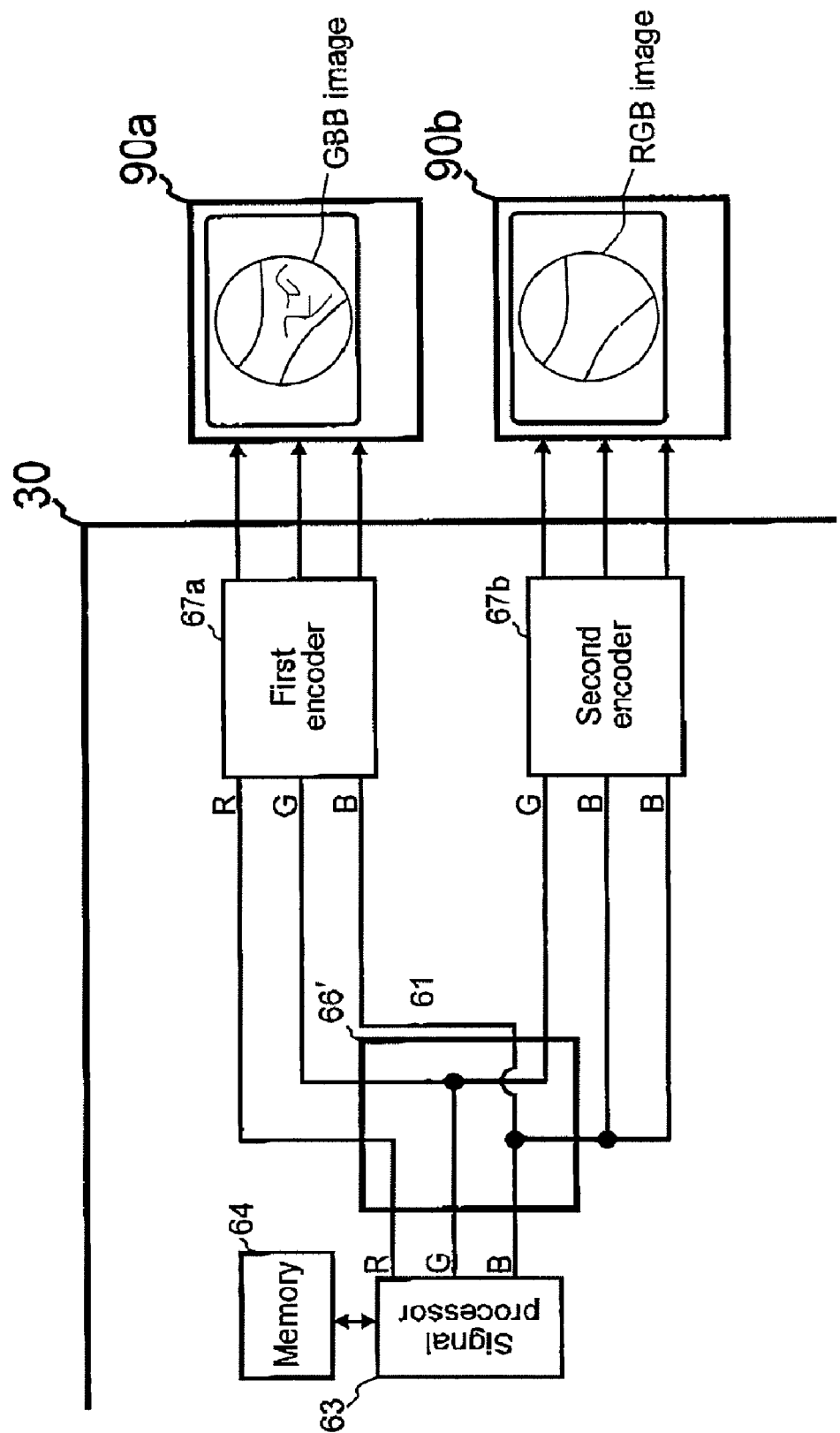
FIG. 7 is a construction diagram of the vicinity of the distributor, when the distributor is used in place of the switcher.

Furthermore, the switcher 66, one encoder 67, and one display 90 are used in the first embodiment, however, a distributor 66', two encoders 67 (a first encoder 67a and a second encoder 67b), and two displays (a first display 90a and a second display 90b) may be alternatively used (see FIG. 7).

The distributor 66' distributes the red, green, and blue signals, outputs the red, green, and blue signals to the first encoder 67a, and outputs the green and blue signals to the second encoder 67b.

The first encoder 67a performs the secondary image processing on the image signal including the red, green, and blue signals from the distributor 66', so as to generate the video signal for displaying the RGB image on the first display 90a, and then outputs the video signal to the first display 90a.

The second encoder 67b performs the secondary image processing on the image signal including the green and blue signals from the distributor 66', so as to generate the video signal for displaying the GBB image on the second display 90b, and then outputs the video signal to the second display 90b.

Furthermore, because the laser beam light whose wavelength is narrow and whose luminous intensity in the narrow wavelength range is strong is used for the illumination light in the first embodiment, the separation of the reflected light for every wavelength can be effectively performed. The light based on the light-emitting diode may be alternatively used.

Therefore, a clearer image can be obtained compared to when the light whose wavelength is wide and whose luminous intensity in the narrow wavelength range is not strong, such as the xenon lamp etc., is used for the illumination light.

Figure 8:
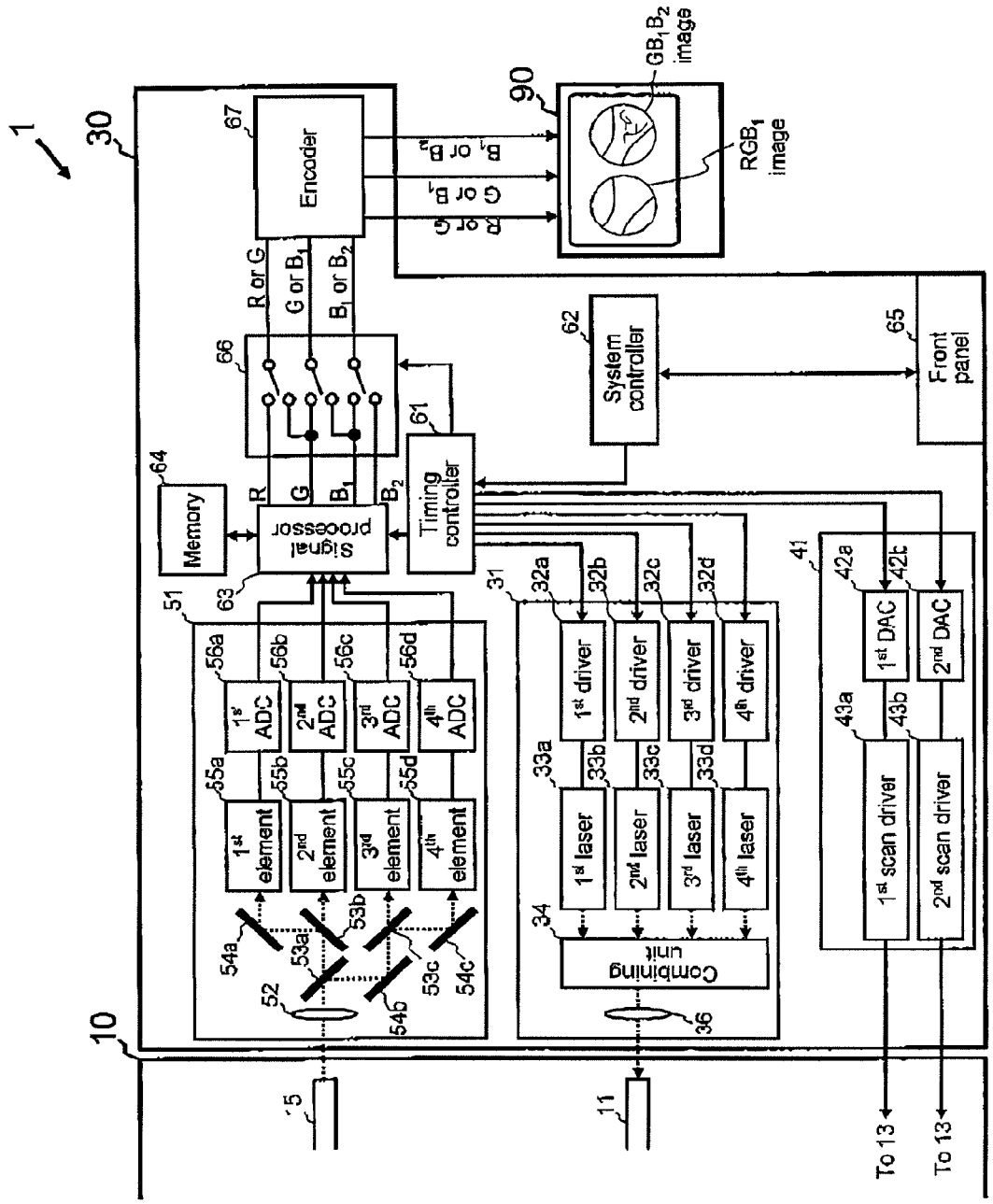
FIG. 8 is a construction diagram of the endoscope system in the second embodiment.
Figure 9:
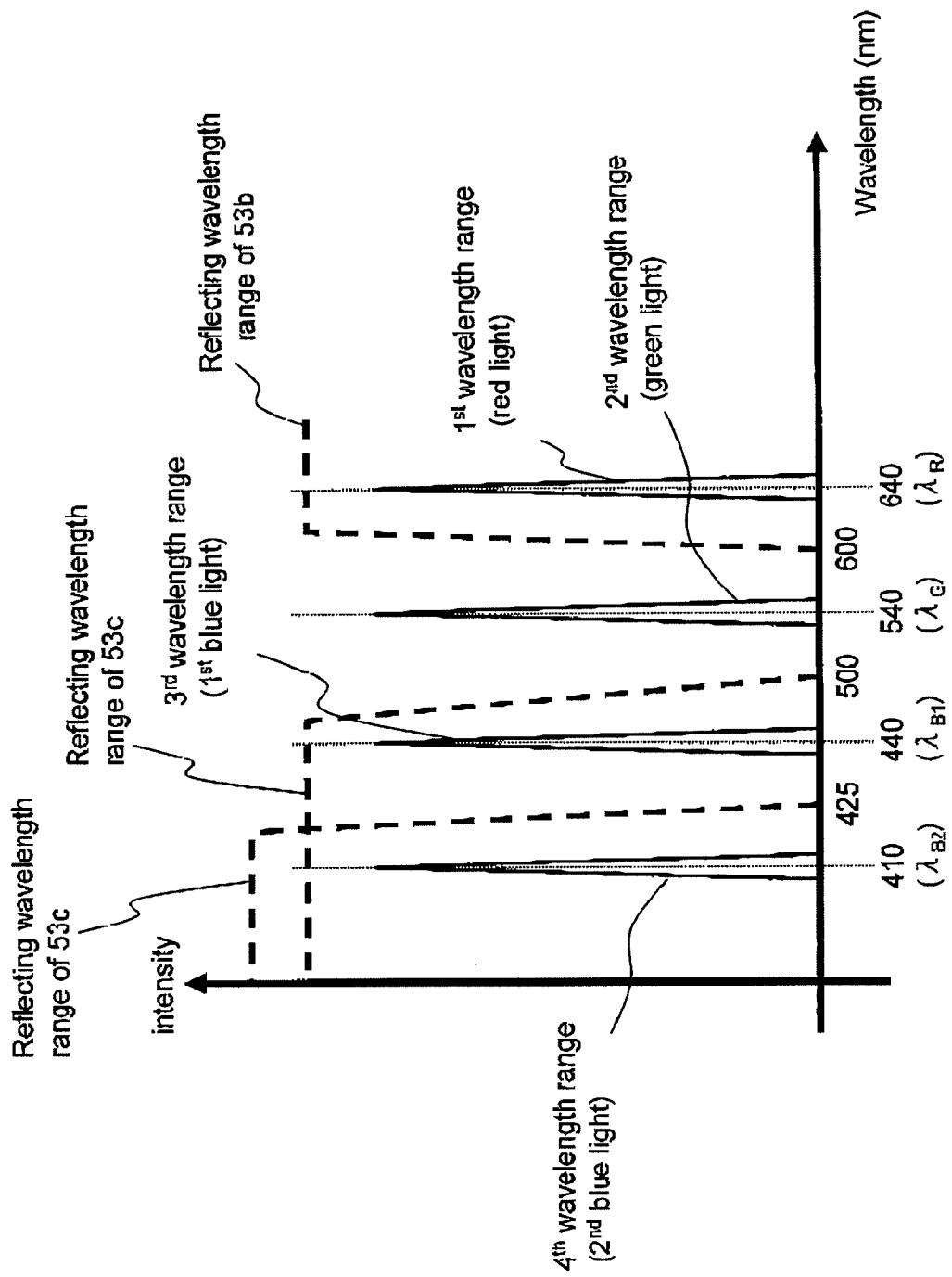
FIG. 9 shows the wavelength ranges of the light output from the first through fourth lasers.

Next, the second embodiment is explained (see FIGS. 8 and 9).

In the first embodiment, the blue signal that is output to the green channel and the blue channel of the encoder 67 includes the same light at the third wavelength range, in order to display the GBB image.

However, in the second embodiment, the wavelength range of the light included in the blue signal that is output to the green channel of the encoder 67 is different from that in the blue signal that is output to the blue channel of the encoder 67, in order to display the $GB_1B_2$ image. The points that differ from the first embodiment are explained next.

In the second embodiment, the light source 31 has a first driver 32a, a second driver 32b, a third driver 32c, a fourth driver 32d, a first laser 33a, a second laser 33b, a third laser 33c, a fourth laser 33d, a combining unit 34, and a first condenser lens 36 for illuminating.

The first laser 33a is a red light laser diode, and emits light in a first wavelength range including a first wavelength $\lambda_R$ on the basis of the control of the timing controller 61, the system controller 62, and the first driver 32a. The first wavelength $\lambda_R$ is about 640 nm, namely, from 630 nm to 650 nm.

The second laser 33b is a green light laser. For example, the second laser 33b may consist of an infrared laser diode together with a wavelength conversion board), and emit the light in a second wavelength range including a second wavelength $\lambda_G$ on the basis of the control of the timing controller 61, the system controller 62, and the second driver 32b. The second wavelength $\lambda_G$ is about 540 nm, namely, from 532 nm to 550 nm.

The third laser 33a is a blue light laser diode, and emits the first blue light in a third wavelength range including a third wavelength $\lambda_{B1}$ on the basis of the control of the timing controller 61, the system controller 62, and the third driver 32c. The third wavelength $\lambda_{B1}$ is about 440 nm (445 nm).

The fourth laser 33d is a blue light laser diode, and emits the second blue light at a fourth wavelength range including a fourth wavelength $\lambda_{B2}$ on the basis of the control of the timing controller 61, the system controller 62, and the fourth driver 32d. The fourth wavelength $\lambda_{B2}$ is about 410 nm (408 nm).

The four wavelength ranges do not overlap.

There are two peak wavelengths at which hemoglobin absorbs light. One is 550 nm, the other is 415 nm. Therefore, when the second wavelength range includes 550 nm or when the fourth wavelength range includes 415 nm, the blood vessel undergoing growth become clear so that an image clearly distinguishing an affected region from a healthy region may be obtained.

The light paths of the first, second, third, and fourth lasers 33a, 33b, 33c, and 33d are combined into one by the combining unit 34.

The resulting white light from the combining unit 34 is condensed by the first condenser lens 36 and is transmitted to the fiber 11.

The light sensor 51 has a second condenser lens 52 for receiving, a first separation mirror 53a, a second separation mirror 53b, a third separation mirror 53c, a first mirror 54a, a second mirror 54b, a third mirror 54c, a first light-sensitive element 55a, a second light-sensitive element 55b, a third light-sensitive element 55c, a fourth light-sensitive element 55d, a first AD converter 56a, a second AD converter 56b, a third AD converter 56c, and a fourth AD converter 56d.

The first separation mirror 53a, the second separation mirror 53b, and the third separation mirror 53c separate light of a predetermined wavelength range; for example, a dichroic mirror.

Short-wavelength light (i.e., blue light of less than 500 nm), in other words, the first blue light including the third wavelength range and the second light including the fourth wavelength range, is reflected by the first separation mirror 53a (see FIG. 9).

The other lights, in other words, the red light including the first wavelength range and the green light including the second wavelength range, pass through the first separation mirror 53a.

Long-wavelength light (i.e., red light of more than 600 nm), in other words, the red light including the first wavelength range, is reflected by the second separation mirror 53b.

The other light, in other words, the green light including the second wavelength range, passes through the second separation mirror 53b.

Short-wavelength light (i.e., blue light less than 425 nm), in other words, the second blue light including the fourth wavelength range, is reflected, by the third separation mirror 53c.

The remaining light, in other words, the first blue light including the third wavelength range, passes through the third separation mirror 53c.

The first light-sensitive element 55a, the second light-sensitive element 55b, the third light-sensitive element 55c, and the fourth light-sensitive element 55d consist of a photodetector such as the photomultiplier tube, etc.

The light transmitted from the fibers 15 is converted to a parallel light beam by the second condenser lens 52.

Then, the red light in the parallel light beam reaches the first light-sensitive element 55a through the first separation mirror 53a, the second separation mirror 53b, and the first mirror 54a.

The green light in the parallel light beam reaches the second light-sensitive element 55b through the first separation mirror 53a and the second separation mirror 53b.

The first blue light in the parallel light beam reaches the third light-sensitive element 55c through the first separation mirror 53a, the second mirror 54b, and the third separation mirror 53c.

The second blue light in the parallel light beam reaches the fourth light-sensitive element 55d through the first separation mirror 53a, the second mirror 54b, the third separation mirror 53c, and the third mirror 54c.

The first light-sensitive element 55a performs the photoelectric conversion on the red light incident on the first light-sensitive element 55a.

The first AD converter 56a performs the AD conversion on the red light incident on the first light-sensitive element 55a after the photoelectric conversion, and then outputs the analog signal of the red light to the signal processor 63.

The second light-sensitive element 55b performs the photoelectric conversion on the green light incident on the second light-sensitive element 55b.

The second AD converter 56b performs the AD conversion on the green light incident on the second light-sensitive element 55b after the photoelectric conversion, and then outputs the analog signal regarding the green light to the signal processor 63.

The third light-sensitive element 55c performs the photoelectric conversion on the first blue light incident on the third light-sensitive element 55c.

The third AD converter 56c performs the AD conversion on the first blue light incident on the third light-sensitive element 55c after the photoelectric conversion, and then outputs the analog signal regarding the first blue light to the signal processor 63.

The fourth light-sensitive element 55d performs the photoelectric conversion on the second blue light incident on the fourth light-sensitive element 55d.

The fourth AD converter 56d performs the AD conversion on the second blue light incident on the fourth light-sensitive element 55d after the photoelectric conversion, and then outputs the analog signal regarding the second blue light to the signal processor 63.

The signal processor 63 reads the image signal temporarily stored in the memory 64, in separate color signals. Specifically, the signal processor 63 reads each the red signal (R signal) based on the red light incident on the first light-sensitive element 55a, the green signal (G signal) based on the green light incident on the second light-sensitive element 55b, the first blue signal ($B_1$ signal) based on the first blue light incident on the third light sensitive element 55c, and the second blue signal ($B_2$ signal) based on the second blue light incident on the fourth light-sensitive element 55d, and then outputs them to the encoder 67 through the switcher 66.

Thereby, the signal processor 63 obtains the red signal based on the red light including the first wavelength range, the green signal based on the green light including the second wavelength range, the first blue signal regarding the first blue light including the third wavelength range, and the second blue signal regarding the second blue light including the fourth wavelength range, on the basis of the light received by the light sensor 51.

The switcher 66 performs the switching operation between a first switching state corresponding to the RGB image display mode and a second switching state corresponding to the GBB image display mode.

In the first switching state (in the RGB image display mode), the red signal, the green signal, and the first blue signal from the signal processor 63 are output to the encoder 67.

In the second switching state (in the GBB image display mode), the green signal, the first blue signal, and the second blue signal, from the signal processor 63 are output to the encoder 67.

The switching operation may be performed by using an electrical switching circuit as shown in FIG. 5, however, it may also be performed through software.

In the RGB image display mode where the $RGB_1$ image based on the red, green, and first blue signals are displayed on the display 90, the red, green, and first blue signals are output from the switcher 66 to the encoder 67. Specifically, the red and green signals are output to the respective channels of the encoder 67, and the first blue signal is output to the blue channel of the encoder 67. Therefore, the second blue signal does not reach the encoder 67.

Moreover, in the RGB imago display mode, the $RGB_1$ image based on the red, green, and first blue signals is used, however, the $RGB_2$ image based on the red, green, and second blue signals may be used.

In the GBB image display mode where the $GB_1B_2$ image based on the green signal, the first blue signal, and the second blue signal is displayed on the display 90, the green signal, the first blue signal, and the second blue signal are output from the switcher 66 to the encoder 67. Specifically, the green signal is output to the red channel of the encoder 67, the first blue signal is output to the green channel, and the second blue signal is output to the blue channel of the encoder 67. Therefore, the red signal does not reach the encoder 67.

In the dual display mode where the $RGB_1$ image and the $GB_1B_2$ image are displayed in parallel on the display 90 (see FIG. 1), the switcher 66 switches to the first switching state during the first half of a display scan line, and to the second switching state during the latter half of the display scan line.

The other constructions in the second embodiment are the same as those in the first embodiment.

Short-wavelength light is reflected near the surface layer of tissue. The depth from the surface of the tissue from which light is reflected varies according to the wavelength of the illumination light. Specifically, when the wavelength of the illumination light is short, the depth from the surface of the tissue from which light is reflected is shallow. When the wavelength of the illumination light is long, the depth from the surface of the tissue from which light is reflected is deep.

Therefore, in the second embodiment that obtains the $CB_1B_2$ image on the basis of the first blue light and the second blue light as opposed to just the first blue light, the tissue image at an intended depth near the surface can be clearly obtained as compared to the first embodiment.

In the first and second embodiments, a full-color scanning fiber endoscope is used for explanation, however, when a narrow light beam, such as a laser beam, etc., is used as the light source, and when the image is obtained with the light being separated into each wavelength range, another endoscope system other than a full-color scanning fiber endoscope may be used.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2008-051625 (filed on Mar. 3, 2000) which is expressly incorporated herein by reference, in its entirety.

The invention claimed is:

1. An endoscope system comprising:
a light source that has a first emitter that emits red light in a first wavelength range including a first wavelength, a second emitter that emits green light in a second wavelength range including a second wavelength, and a third emitter that emits blue light in a third wavelength range including a third wavelength, and outputs the light from said first emitter, said second emitter, and said third emitter, said second wavelength being shorter than said first wavelength, said third wavelength being shorter than said second wavelength, said first wavelength range not overlapping said second wavelength range, and said second wavelength range not overlapping said third wavelength range;

a light sensor that receives the light of said light source as reflected by the photographic subject, with the light being separated into each wavelength range;

a signal processor that obtains a red signal based on the light including said first wavelength range, a green signal based on the light including said second wavelength range, and a blue signal based on the light including said third wavelength range, on the basis of the light received by said light sensor;

a video-signal generator that generates a video signal based on at least one of said red signal, said green signal, and said blue signal, obtained by said signal processor; and a switcher that switches between a first switching state and a second switching state;

said red signal, said green signal, and said blue signal being output to said video-signal generator in said first switching state;

said green signal and said blue signal being output to said video-signal generator in said second switching state;

said switcher outputs said red signal to a red channel of said video-signal generator, outputs said green signal to a green channel of said video-signal generator, and outputs said blue signal to a blue channel of said video-signal generator, in said first switching state; and said switcher outputs said green signal to said red channel, and outputs said blue signal to said green channel and said blue channel, in said second switching state.

2. The endoscope system according to claim 1, wherein said at least one of said second wavelength range and said third wavelength range includes a peak wavelength at which hemoglobin absorbs light.

3. The endo scope system according to claim 1, wherein said switcher switches to said first switching state during the first half of a display scan line, and to said second switching state during the latter half of said display scan line.

4. An endoscope system, comprising:

a light source that has a first emitter that emits red light in a first wavelength range including a first wavelength, a second emitter that emits green light in a second wavelength range including a second wavelength, and a third emitter that emits blue light in a third wavelength range including a third wavelength, and outputs the light from said first, second, and third emitters, said second wavelength being shorter than said first wavelength, said third wavelength being shorter than said second wavelength, said first wavelength range not overlapping said second wavelength range, and said second wavelength range not overlapping said third wavelength range;

a light sensor that receives the light of said light source as reflected by the photographic subject, with the light being separated into each wavelength range;

a signal processor that obtains a red signal based on the light including said first wavelength range, a green signal based on the light including said second wavelength range, and a blue signal based on the light including said third wavelength range, on the basis of the light received by said light sensor;

a first video-signal generator that generates video signals based on said red signal, said green signal, and said blue signal;

a second video-signal generator that generates video signals based on only said green signal and said blue signal; and a distributor that outputs said red signal, said green signal, and said blue signal to said first video-signal generator, and outputs said green signal and said blue signal to said second video-signal generator.

5. An endo scope system, comprising:

a light source that has a first emitter that emits red light in a first wavelength range including a first wavelength, a second emitter that emits green light in a second wavelength range including a second wavelength, a third emitter that emits first blue light in a third wavelength range including a third wavelength, and a fourth emitter that emits second blue light in a fourth wavelength range including a fourth wavelength, and outputs the light from said first, second, third, and fourth emitters, said second wavelength being shorter than said first wavelength, said third wavelength being shorter than said second wavelength, said fourth wavelength being shorter than said third wavelength, said first wavelength range not overlapping said second wavelength range, said second wavelength range not overlapping said third wavelength range, and said third wavelength range not overlapping said fourth wavelength range;

a light sensor that receives the light of the photographic subject based on the light from said light source, with the light being separated into each wavelength range;

a signal processor that obtains a red signal based on the light including said first wavelength range, a green signal based on the light including said second wavelength range, a first blue signal based on the light including said third wavelength range, and a second blue signal based on the light including said fourth wavelength range, on the basis of the light received by said light sensor;

a video-signal generator that generates a video signal based on at least one of said red signal, said green signal, said first blue signal, and said second blue signal, obtained by said signal processor; and a switcher that switches between a first switching state and a second switching state;

said green signal, and one of said first blue signal and said second blue signal, being output to said video-signal generator in said first switching state; and said green signal, said first blue signal, and said second blue signal being output to said video-signal generator in said second switching state.

* * * * *